United States Patent [19]

Small, Jr. et al.

[11] Patent Number: 5,160,650

[45] Date of Patent: * Nov. 3, 1992

[54] MONOALKYLAMINE COMPLEXES OF BORATED HIGHER CARBON NUMBER ALKYL CATECHOLS AND LUBRICATING OIL COMPOSITIONS CONTAINING THE SAME

[75] Inventors: Vernon R. Small, Jr., Rodeo; Thomas V. Liston, San Rafael; Anatoli Onopchenko, Concord, all of Calif.

[73] Assignee: Chevron Research and Technology Company, San Francisco, Calif.

[*] Notice: The portion of the term of this patent subsequent to Aug. 25, 2009 has been disclaimed.

[21] Appl. No.: 669,265

[22] Filed: Mar. 14, 1991

Related U.S. Application Data

[63] Continuation-in-part of Ser. No. 413,420, Sep. 27, 1989, abandoned.

[30] Foreign Application Priority Data

Sep. 14, 1990 [WO] PCT Int'l Appl. ... PCT/US90/05138

[51] Int. Cl.$^5$ .......................................... C10M 139/00
[52] U.S. Cl. ................................. 252/49.6; 558/290; 558/291
[58] Field of Search ................. 252/49.6; 558/290, 291

[56] References Cited

U.S. PATENT DOCUMENTS

| | | | |
|---|---|---|---|
| 2,344,393 | 3/1944 | Cook et al. | 252/32.7 E |
| 2,497,521 | 2/1950 | Trautman | 252/49.6 |
| 2,795,548 | 6/1957 | Thomas et al. | 252/74 |
| 2,883,412 | 4/1959 | Lowe | 252/49.6 |
| 3,065,236 | 11/1962 | Young et al. | 260/293 |
| 3,133,800 | 5/1964 | DeGray et al. | 44/317 |
| 3,361,672 | 1/1968 | Andress et al. | 252/49.6 |
| 3,442,807 | 5/1969 | Law | 252/49.6 |
| 4,328,113 | 5/1982 | Horodysky et al. | 252/49.6 |
| 4,611,013 | 9/1986 | Ashida | 558/290 |
| 4,629,577 | 12/1986 | Liston | 252/32.7 E |
| 4,629,578 | 12/1986 | Liston | 252/49.6 |
| 4,632,771 | 12/1986 | Liston et al. | 252/32.7 E |
| 4,643,838 | 2/1987 | Liston et al. | 252/49.6 |
| 4,781,850 | 11/1988 | Doner et al. | 252/49.6 |
| 4,927,553 | 5/1990 | Wright et al. | 252/49.6 |
| 4,975,211 | 12/1990 | Small, Jr. et al. | 252/49.6 |
| 5,061,390 | 10/1991 | Small, Jr. et al. | 252/49.6 |

*Primary Examiner*—Jerry Johnson
*Attorney, Agent, or Firm*—R. C. Gaffney; J. A. Hagenah

[57] ABSTRACT

Borated alkyl catechols can be stabilized by the addition of certain defined monoalkylamines.

Lubricating oils containing a borated alkyl catechol-monoalkylamine complex are effective in reducing oxidation, wear and deposits in an internal combustion engine.

41 Claims, No Drawings

MONOALKYLAMINE COMPLEXES OF BORATED HIGHER CARBON NUMBER ALKYL CATECHOLS AND LUBRICATING OIL COMPOSITIONS CONTAINING THE SAME

CROSS-REFERENCES TO RELATED APPLICATIONS

This application is a continuation-in-part of U.S. Ser. No. 413,420, filed Sept. 27, 1989, now abandoned.

BACKGROUND OF THE INVENTION

1. Field of the Invention

This invention is concerned with the product obtained by reacting a borated alkyl catechol with certain monoalkylamines and the use of said product in lubricant compositions.

2. State of the Art

Wear and deposits limit the useful life of automobile and truck engines.

Thus, there is a great need to find lubricants that reduce the oxidation, wear and deposits in the engine, thus increasing the lifetime of the engine.

U.S. Pat. No. 2,795,548 discloses the use of lubricating oil compositions containing a borated alkyl catechol The oil compositions are useful in the crankcase of an internal combustion engine in order to reduce oxidation of the oil and corrosion of the metal parts of the engine.

There is a problem with the use of borated alkyl catechols in lubricating oils since they are sensitive to moisture and hydrolyze readily. The hydrolysis leads to haze and/or precipitate formation which must be filtered out prior to use. It has now been found that the borated alkyl catechols may be stabilized against hydrolysis by complexing the borated alkyl catechol with certain monoalkylamines.

More importantly, lubricating the crankcase of an internal combustion engine with a lubricating oil containing the reaction product of a borated alkyl catechol and certain monoalkylamines reduce oxidation and wear in gasoline engines and deposits in diesel engines U.S. Pat. No. 2,497,521 to Trautman relates to the use of amine salts of boro-diol complexes in hydrocarbon oil compositions. The amine salts of the boro-diol complexes are useful as stabilizing agents, i.e., antioxidants. The described boro-diol complexes include diols selected from the group consisting of glycols and polyhydroxy benzenes, including catechol Catechol is a small polar compound which has poor solubility in essentially non-polar base oils under ambient conditions. The use of long chain alkyl groups on the alkyl catechols to enhance its solubility and compatibility in a base oil is not taught in Trautman. A wide range of amines to prepare the salts is taught; indeed "any organic amine may be employed" (Col. 3, lines 51–71).

A recent patent (U.S. Patent No. 4,328,113) assigned to Mobil Oil Corporation teaches the use of high molecular weight (C-8+) amines and diamines with boric acid itself for use as grease and lubricating oil additives. The use of borated catechols let alone borated alkylated catechols is not taught in this patent.

U.S. Pat. No. 4,655,948 to Doner et al. discloses grease compositions having increased dropping points Among the compositions described are mixtures of a hydroxy-containing thickener and borated catechol compounds having the structure:

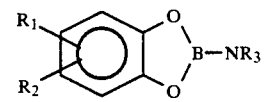

where $R_1$ and $R_2$ are each H or $C_1$ to $C_{40}$; and where $R_3$ is a $C_1$ to $C_{40}$ hydrocarbyl and can contain, additionally, oxygen, sulfur and/or nitrogen-containing moieties.

The catechol amine borate compounds of Doner et al., as indicated in the above formula, are described as trigonal boron compounds having nitrogen-boron single bonds formed by driving the condensation reaction to completion via the azeotropic removal of water. A variety of useful amines are described in Column 2 lines 62, et seq. Although some amines listed contain secondary amine structures, the common link in all amines is the presence of primary amine structures. It is also to be noted that Doner's list of amines are all high molecular weight aliphatic amines, e.g., oleyl amine or are aromatic, i.e., aniline. Primary amines such as monoalkylamines with short alkyl chains are not specifically described.

U.S. Pat. Nos. 3,133,800 and 3,203,971 to De Gray et al. disclose glycol borate amine compounds of aliphatic saturated glycols, useful as fuel additives, for example as deicing agents and bactericides. Useful amines, among others, include those with alkyl groups having from 3 to 20 carbon atoms U.S. Pat. No. 2,883,412 to Lowe discloses p-xylylene diamine salts of glycol boric acids having superior corrosion inhibiting properties. Among the compounds disclosed are p-xylylene diamine adducts of alkyl catechol borates, such as derived from butyl and cetyl catechol (Col. 3 lines 61–68).

Reactions of trialkyl borates with amines, including diethylamine, triethylamine, cyclohexylamine, and ethylenediamine are described by Wilson in *J. Chem. Soc. Dalton,* 1973, pp. 1628 and by Colclough et al. in *J. Chem. Soc.,* 1955, pp. 907. The latter, in addition, describes reactions of triphenylborates with amines and on page 909 shows that attempts to prepare a diethylamine product resulted in a product that was low in amine content, but dry ethylamine formed complex with triphenylborate. Moreover, even the much more stable pyridine complex of triphenylborate described in this paper hydrolyzed completely in moist air in 5 days. These references do not mention alkyl catechol derivatives However, Kuremel et al. in *J. Amer. Chem. Soc.* 78, pp. 4572 (1956) does talk about catechol-boric acid-pyridine complexes. Kuremel shows on page 4574 that "there is complete dissociation of the complexes into their substituents (pyrocatechol, pyridine, and boric acid) in alcoholic solution". Alkyl catechols were not mentioned.

U.S. Pat. No. 4,629,578 to T. V. Liston teaches that a complex of borated alkyl catechol with a succinimide is useful in lubricant compositions. The succinimide additives of Liston are effective in stabilizing the borated alkyl catechols to hydrolysis. Preferred succinimides have a number average molecular weight of about 600 to about 1,500 (Column 4, lines 12, et seq.). These high molecular weight succinimides effectively dilute the concentration of the desired borated alkyl catechols. In addition, using high molecular weight succinimides for hydrolytic stabilization results in higher transportation costs for the additive, and a loss of flexibility since their use is limited to formulations containing succinimides as dispersants, due to compatibility problems.

Previously, it was believed that low molecular weight amines would not be useful in lubricants subjected to high temperatures, e.g., >100° C. because of the volatility of the amines; that is, it was believed that the amines would be lost during use and not provide ongoing stabilization against hydrolysis. Indeed, all prior art examples show lubricant-type compositions with higher molecular weight amines than monoalkylamines of this invention.

We have now surprisingly found that certain monoalkylamine-borated alkyl catechol complexes are stable with respect to decomposition to starting materials under "in use" conditions. The certain monoalkylamine stabilized alkyl borated catechols of this invention passed the L-38 engine test (with a score of about 30 mg weight loss), where the presence of "free" amine such as oleyl amine under these conditions would give very high (300–600 mg) weight losses due to corrosion of the copper and lead bearings. Also, calorimetry data (DSC) shows that the monoalkylamine stabilized alkyl borated catechols of this invention are stable to about 200.C, which is significantly above the sump temperature of a gasoline engine The thermal stability of catechol boron amine complexes is not predictable. For example, dimethylamine does not form a stable complex with alkylated borated catechols nor does diisopropyl amine. The interaction of steric effects, nitrogen basicity and boron electrophilicity all come into play. These factors affect the equilibrium between the reactants and the products and make predictions of thermal stability impossible. One also cannot predict hydrolytic stability, which may or may not be related to thermal stability.

The problem, therefore, addressed and solved by this invention is how to hydrolytically stabilize borated alkyl catechols so as to achieve a higher concentration of boron per pound of the borated alkyl catechols. This is achieved by complexing such catechols and stabilizing the same with a low molecular weight stabilizing material, i.e., certain monoalkylamines.

SUMMARY OF THE INVENTION

According to the present invention, lubricating oils are provided which reduce wear, oxidation and deposits and are especially useful in the crankcase of internal combustion engines. The reduced wear, oxidation and deposits result from the addition to the lubricating oil of small amounts of a complex prepared by reacting a borated alkyl catechol and one or more monoalkylamines having from 2 to 10 carbon atoms and from 0 to 3 hydroxyl groups Preferred monoalkylamines have the formula:

where R' is an aliphatic hydrocarbon radical having from 2 to 10 carbon atoms, preferably 2 to 6 carbon atoms, and which optionally contains from one to three hydroxyl groups; or an alicyclic hydrocarbon radical having 5 or 6 carbons (hereinafter defined "monoalkylamine(s)").

Suitable monoalkylamines include 2-ethyl-hexylamine; ethylamine; n-butylamine; hexylamine; cyclohexylamine, hydroxyethylamine; hydroxypropylamine; and dihydroxypropylamine. The amines can be used alone or a mixture of amines can be employed.

Unsuitable amines include ammonia, methylamine and benzylamine.

The method of preparation of the defined monoalkylamines forms no part of this invention. Such defined monoalkylamines are available in the marketplace or can be prepared by methods known in the art.

Thus, in one aspect, this invention relates to a lubricating oil composition comprising an oil of lubricating viscosity and a minor amount of a hydrolytically stable complex of a borated alkyl catechol and the defined monoalkylamines.

In another aspect, this invention relates to a concentrate of a neutral carrier oil containing from 5 to 80 weight percent (based on the neutral oil) of the stabilized defined monoalkylamine-borated alkyl catechol complexes of this invention.

These complexes may be readily prepared by contacting (a) a borated alkyl catechol and (b) a defined monoalkylamine under conditions wherein a complex is formed between the monoalkylamine and the borated alkyl catechol, the amount of the defined monoalkylamine being sufficient to stabilize said borated alkyl Catechol against hydrolysis.

Other additives may also be present in the lubricating oils in order to obtain a proper balance of properties such as dispersancy, corrosion, wear and oxidation inhibition which are critical for the proper operation of an internal combustion engine.

In still another aspect of this invention, there is provided a method for reducing wear, oxidation and deposits in an internal combustion engine by utilizing the lubricating oil composition described above. Specifically, improvements in deposits of from 10%-50% may be obtained by employing the composition of this invention This deposit improvement can be obtained in compression-ignition engines, that is, diesel engines. Improvements in viscosity control of 25%-50% can be obtained in spark-ignition engines, that is, gasoline engines. That is, lubricating oil compositions containing the borated alkyl catechol-defined monoalkylamine complexes of this invention have been found additionally to possess (1) antioxidant properties in gasoline engines and (2) diesel deposit inhibition when employed in diesel engines.

The borated alkyl catechols may be prepared by borating an alkyl catechol with boric acid with removal of the water of reaction. Typically, there is sufficient boron present such that each boron will react with about 2 to 3 hydroxyl groups present in the reaction mixture. (See Formulas IV, V and VI below.)

The reaction may be carried out at a temperature in the range of 60° C.–135° C. or higher, in the absence or presence of any suitable organic solvent which forms an azeotrope with water such as benzene, xylenes, toluene and the like.

Depending on the ratio of alkyl catechol to boron, the composition of the borated alkyl catechol, and therefore the composition of the amine adduct varies. It is believed that at a 3:2 ratio of alkyl catechol to boron and a 1:1 ratio of boron to nitrogen, the predominant product has a structure like Formula V below. At a 1:1 ratio of alkyl catechol to boron and a 1:1 ratio of boron to nitrogen the predominant product has a structure like Formula VI below.

The alkyl catechols or mixtures thereof which may be used to prepare the borated alkyl catechols used in this invention are preferably mixtures of monoalkyl and dialkyl catechols. The monoalkyl catechols are preferably of Formula I

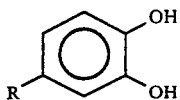
Formula I wherein R is alkyl containing at least 10 carbon atoms; usually 10 to about 60 carbon atoms and preferably from 10 to 30 carbon atoms, more preferably from 18 to 24 carbon atoms and even more preferably 20 to 24 carbon atoms. Also, up to 60% by weight but preferably less than 40% by weight of the monoalkyl catechols may have the R group in a position adjacent or ortho to one of the hydroxy groups and have the Formula II

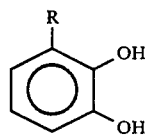
Formula II wherein R is as defined above.

The dialkyl catechols which may be used to prepare a mixture of borated alkyl catechols of this invention are generally of Formula III

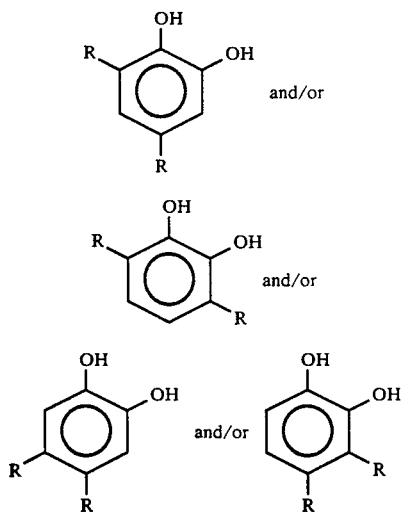
Formula III wherein R is as defined above and the two R groups can be the same or different. Trialkyl catechols may also be employed although they are not preferred.

As noted above, the alkyl group on the alkyl catechol contains at least 10 carbon atoms. Suitably the alkyl group can have from 10 to 60 carbon atoms or more and, of course, mixtures of such alkyl groups can be employed.

Among the alkyl catechols which may be employed are decyl catechol, undecyl catechol, dodecyl catechol, tetradecyl catechol, pentadecyl catechol, hexadecyl catechol, octadecyl catechol, eicosyl catechol, hexacosyl catechol, triacontyl catechol, tetracontyl catechol, pentacontyl catechol, hexacontyl catechol and the like. Also, a mixture of alkyl catechols may be employed such as a mixture of $C_{14}$–$C_{18}$ alkyl catechols, a mixture of $C_{18}$–$C_{24}$ alkyl catechols, a mixture of $C_{20}$–$C_{24}$ alkyl catechols, a mixture of $C_{16}$–$C_{26}$ alkyl catechols or a mixture of $C_{32}$ ∝ $C_{60}$ alkyl catechols.

Higher carbon number alkyl groups, such as those having greater than 30 carbon atoms, are preferably derived from "alpha olefin oligomer(s)." Such higher carbon number alkyl groups generally contain 32 to 60 carbon atoms, preferably to 50 carbon atoms.

The term "alpha olefin oligomer" as used herein refers to alpha olefin dimers, trimers, tetramers and pentamers or mixtures thereof which have from 32 to 60 carbon atoms. Such alpha olefin oligomers can be prepared or derived from $C_8$ to $C_{20}$ alpha olefins, preferably $C_{10}$ to $C_{14}$ alpha olefins, or mixtures of such alpha olefins. Examples of alpha olefin oligomers include $C_8$ tetramers and pentamers; $C_{10}$ tetramers and pentamers; $C_{12}$ trimers and tetramers; $C_{14}$ trimers; $C_{16}$ dimers and trimers; $C_{18}$ dimers; and $C_{20}$ dimers. Alpha olefin oligomers useful in preparing alkyl catechols with higher carbon number alkyl groups contain preferably 32 to 60 carbon, atoms, more preferably 36 to 5..0carbon atoms.

Alpha olefin oligomers can be single carbon number oligomers such as the tetramer of 1-decene, tetracontene ($C_{40}$). Generally, however, the oligomers used to prepare alkyl catechols having higher carbon number alkyl groups are mixtures of alpha olefin dimers, trimers, tetramers, and the like Such oligomer mixtures can be described by their "number average carbon number." The "number average carbon number" is determined by multiplying the number of carbon atoms of each oligomer in the mixture by the weight percent of that oligomer and then adding the products. For example, the number average carbon number of an oligomer mixture containing 10% by weigh $C_{30}$, 50% by weigh $C_{40}$ and 40% by weight $C_{50}$ is $[(30 \times 0.10) + (40 \times 0.50) + (50 \times 0.40)]$, or 43. Oligomer mixtures useful in the present invention preferably have a number average carbon number of about 35 to 45.

The alpha olefin oligomers used herein are prepared by methods well-known in the art. For example, these oligomers can be prepared using boron trifluoride catalysts as described in U.S. Pat. Nos. 4,238,343 and 4,045,507, and in Onopchenko, et al, *BF3-Catalyzed Oligomerization of Alkenes (Structure, Mechanisms and Properties)*, 183rd ACS Natl. Meet. (Las Vegas, March 1982), *Ind. Eng. Chem , Prod. Res. Dev.*, 22(2), 182-91 (June 1983).

The alkyl catechols of Formulae I, II and III may be prepared by reacting an olefin having at least 10 carbon atoms, such as a branched olefin or straight-chain alpha olefin (or mixtures of such olefins) with catechol in the presence of a sulfonic acid catalyst at a temperature of from about 60° C.-200° C., preferably 125° C.-180° C., and most preferably 130° C.-150° C. in an essentially inert solvent at atmospheric pressure. Although alkylation of catechol can be carried out neat, in absence of solvents, the use of solvents, particularly in a batch reactor greatly facilitates the process due to better contact of the reactants, improved filtration, etc. Examples of the inert solvents include benzene, toluene, chlorobenzene and Chevron 250 Thinner which is a mixture of aromatics, paraffins and naphthenes.

The term "branched olefin" means that branching occur at the double bond, i.e., vinylidene olefins or trisubstituted olefins. The term "straight-chain alpha olefin" means that the alpha olefin contains little (less than about 20%) or no branching at the double bond or elsewhere.

Monoalkyl catechols are preferred. A product which is predominantly monoalkyl catechol may be prepared by using molar ratios of reactants (catechol and alkylating olefin) and preferably a 10% molar excess of branched olefin or alpha olefin over catechol is used. When used at molar ratios, the resulting products are generally predominantly monoalkyl catechols but do contain some amounts of dialkyl catechol. A molar excess of catechol (e.g. two equivalents of catechol for each equivalent of olefin) can be used in order to enhance monoalkylation if predominantly monoalkyl catechol is desired. Predominantly dialkyl catechols may be prepared by employing a molar excess of olefin, such as two equivalents of the same or different olefin per equivalent of catechol.

Dialkyl catechols are also useful in this invention. A typical weight ratio of monoalkyl to dialkyl catechol is in the range of 1:3 to 3:1.

Use of a branched olefin results in a greater proportion of alkyl catechols of Formula I than use of straight-chain alpha olefins. Use of such branched olefins generally results in greater than 90% alkyl catechol of Formula I and less than 10% alkyl catechol of Formula II. On the other hand, the use of a straight-chain alpha olefin generally results in approximately 50% of alkyl catechols of Formula I and 50% of Formula II In a case of $C_{20}$–$C_{24}$ olefin mixture, for example, containing 20% branching, the corresponding alkyl catechols will comprise about 60% of Formula I and 40% of Formula II. When the same or different olefin mixture contains 50% branching, the corresponding alkyl catechols will comprise approximately 70% of Formula I and 30% of Formula II.

The exact structure of the complex of this invention is not known for certain. However, while not limiting this invention to any theory, it is believed that the compounds of this invention have a tetrahedral boron atom with three B—O bonds. The boron is either complexed to the nitrogen atom in the monoalkylamine via dative bonding, or is present as a salt.

Tetrahedral Boron

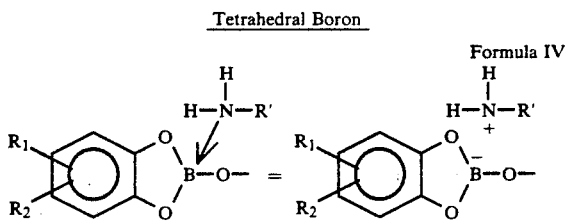

wherein $R_1$ and $R_2$ can be the same or different and each is defined the same as R hereinabove. Formula IV illustrates dative bonding.

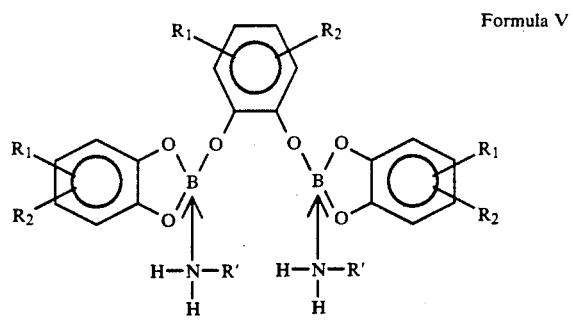

Formula V is a b 3:2 catechol to boron complex.

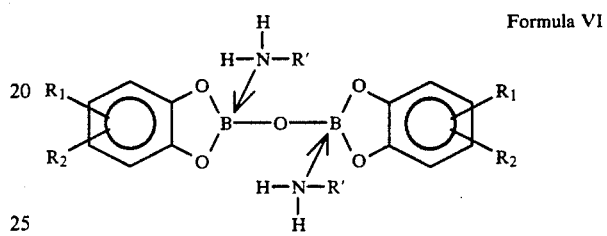

Formula VI is a 1:1 catechol to boron complex.

A borated alkyl catechol having a 3:2 mole ratio of catechol to boron (Formula V) or a 1:1 mole ratio of catechol to boron (Formula VI) is a function of the mole ratio of catechol to boron as noted above. The only two products that are believed to be present are the 1:1 and 3:2 products of Formulas V and VI. Nevertheless, due to equilibrium considerations, the product most likely is a mixture of the 1:1 and 3:2 complexes in varying proportions depending on the stoichiometry used. We have found that a 3:2 product is just as effective in a Sequence IIID test as the 1:1 product. It is thus preferred for cost and handling reasons that the borated alkyl catechol predominate in the 3:2 product and, more preferably, be substantially only the 3:2 product, i.e., that the product be made using a mole ratio of alkyl catechol to boron of about 3:2.

The complex may be formed by reacting the borated alkyl catechol and the defined monoalkylamine together neat at a temperature above the melting point of the mixture of reactants and below the decomposition temperature, or at a suitable temperature in a diluent in which both reactants are soluble. Suitable temperatures can be about 30° C. to 100° C., preferably about 50° C. For example, the reactants may be combined in the proper ratio in the absence of a solvent to form an homogeneous product or the reactants may be combined in the proper ratio in a solvent such as toluene or benzene, xylenes, chlorobenzene, or thinner, and the solvent then stripped off. The complex formed by either technique may then be added to the oil. Most defined monoalkylamine complexes of borated alkyl catechols are either liquids at room temperature, or low melting solids (m.p. 30° C.–40° C.) depending on the composition of their isomers and the purity of the product. Alternatively, the complex may be prepared in a lubricating oil as a concentrate containing from about 5 to 80% by weight of the complex, which concentrate may be added in appropriate amounts to the lubricating oil in which it is to be used or the complex may be prepared directly in the lubricating oil in which it is to be used.

The diluent is preferably inert to the reactants and products formed, and is used in an amount sufficient to ensure solubility of the reactants and to enable the mixture to be efficiently stirred.

Temperatures for preparing the complex may be in the range of from 20° C.-200° C. and preferably 25° C.-60° C. and under sufficient pressure to maintain the defined monoalkylamine in the liquid phase. The most preferred temperatures depend on whether the complex is prepared neat or in a diluent, i.e., higher temperatures may be used when a solvent is employed.

An effective amount of defined monoalkylamine is added in order to stabilize the borated alkyl catechols against hydrolysis. In general, mole ratios of the defined monoalkylamine to boron used to form the complex are in the range of 0.8:1 to 1.1:1, and preferably from 0.9:1 to 1:1, and most preferably 1:1. This latter ratio is preferred if the complex is made and/or stored neat or in the absence of solvent or lubricating oil and under atmospheric conditions. Higher amounts of the defined monoalkylamine can be used but provide no advantages. However, normally excess amine is added to insure complete stabilization and unreacted amine is recovered and recycled.

As used herein, the term "stabilized against hydrolysis" means that the borated alkyl catechol-monoalkylamine complex does not "skin-over" or form a precipitate due to the hydrolysis of the borated catechol for a period of at least one week, preferably three months, when stored at room temperature ($\approx 15°-25°$ C.) and ambient humidity, i.e., no observable or measurable free boric acid is formed. By a stabilizing amount of amine is meant that amount to stabilize the borated alkyl catechol against hydrolysis.

The amount of the complex required to be effective for reducing wear, oxidation and deposits in lubricating oil compositions is a minor amount and may range from 0.05% to 20% by weight. However, in the preferred embodiment, it is desirable to add sufficient complex so that the amount of borated catechol is added at a range from 0.1% to about 4% by weight of the total lubricant composition and preferably is present in the range from 0.2% to 2% by weight and most preferably 0.5% to 1%. The monoalkylamine is present in the complex of the invention in an amount effective to stabilize the borated alkyl catechol against hydrolysis and which allows the borated alkyl catechol to function as an effective oxidation and deposit reducing agent.

The defined monoalkylamine-borated alkyl catechol complexes of this invention can be added to a lubricating oil (or can be made in the lubricating oil). In addition, it is contemplated that the complexes of this invention can be sold as a concentrate in a neutral oil with or without other ingredients such as dispersants, antirust agents, etc. The concentrate can therefore comprise a complex of a borated alkyl catechol and an amount to hydrolytically stabilize the borated alkyl catechol of monoalkylamine plus a neutral carrier oil. The weight percent of the defined monoalkylamine stabilized borated alkyl catechol in the concentrate is usually from 5 to 80 based on the weight of neutral carrier oil, typically 10 to 60. The term "neutral oil" is well known in the art, such as those neutral oils made commercially which have a viscosity in the lubricating oil range, such as 100 neutral oils, 200 neutral oils, etc.

In general, the complexes of this invention may also be used in combination with other additive agents in conventinoal amounts for their known purpose.

For example, for application in modern crankcase lubricants, the base composition described above will be formulated with supplementary additives to provide the necessary stability, detergency, dispersancy, antiwear and anticorrosion properties.

Thus, as another embodiment of this invention, the lubricating oils which contain the complexes prepared by reacting the borated alkyl catechols and the defined monoalkylamine may also contain an alkali or alkaline earth metal hydrocarbyl sulfonate, an alkali or alkaline earth metal phenate, and Group II metal salt dihydrocarbyl dithiophosphate, and conventional viscosity index improvers.

The alkali or alkaline earth metal hydrocarbyl sulfonates may be either petroleum sulfonate, synthetically alkylated aromatic sulfonates, or aliphatic sulfonates such as those derived from polyisobutylene. One of the more important functions of the sulfonates is to act as a detergent and dispersant. These sulfonates are well known in the art. The hydrocarbyl group must have a sufficient number of carbon atoms to render the sulfonate molecule oil soluble. Preferably, teh hydrocarbyl portion has at least 20 carbon atoms and may be aromatic or aliphatic, but is usually alkylaromatic. Most preferred for use are calcium, magnesium or barium sulfonates which are aromatic in character. Certian sulfonates are typically prepared by sulfonating a petroleum fraction having aromatic groups, usually mono- or dialkylbenzene groups, and then forming the metal salt of the sulfonic acid material. Other feedstocks used for preparing these sulfonates include synthetically alkylated benzenes and aliphatic hydrocarbons prepared by polymerizing a mono- or diolefin, for example, a polyisobutenyl group prepared by polymerizing isobutene. The metallic salts are formed directly or by metathesis using well-known procedures.

The sulfonates may be neutral or overbased having base numbers up to about 400 mg of KOH per gram of sample or more. Carbon dioxide and calcium hydroxide or oxide are the most commonly used material to produce the basic or overbased sulfonates. Mixtures of neutral and overbased sulfonates may be used. The sulfonates are ordinarily used so as to provide from 0.3% to 10% by weight of the total composition. Preferably, the neutral sulfonates are present from 0.4% to 5% by weight of the total composition and the overbased sulfonates are present from 0.3% to 3% by weight of the total composition.

The phenates for use in this invention are those conventional products which are the alkali or alkaline earth metal salts of alkylated phenols One of the functions of the phenates is to act as a detergent and dispersant. Among other things, it prevents the deposit of contaminants formed during high temperature operation of the engine. The phenols may be mono- or polyalkylated.

The alkyl portion of the alkyl phenate is present to lend oil solubility to the phenate. The alkyl portion can be obtained from naturally occurring or synthetic sources. Naturally occurring sources include petroleum hydrocarbons such as white oil and wax. Being derived from petroleum, the hydrocarbon moiety is a mixture of different hydrocarbyl groups, the specific composition of which depends upon the particular oil stock which was used as a starting material Suitable synthetic sources include various commercially available alkenes and alkane derivatives which, when reacted with the phenol, yield an alkylphenol. Suitable radicals obtained include butyl, hexyl, octyl, decyl, dodecyl, hexadecyl, eicosyl, triacontyl, and the like. Other suitable synthetic sources of the alkyl radical include olefin polymers such as polypropylene, polybutylene, polyisobutylene and the like.

The alkyl group of the alkyl phenate can be straight-chained or branched-chained, saturated or unsaturated (if unsaturated, preferably containing not more than 2 and generally not more than 1 site of olefinic unsaturation). The alkyl radicals will generally contain from 4 to 30 carbon atoms. Generally, when the phenol is monoalkyl-substituted, the alkyl radical should contain at least 8 carbon atoms. The phenate may be sulfurized if desired. It may be either neutral or overbased and if overbased will have a base number of up to 200 to 300 mg of KOH per gram of sample or more. Mixtures of neutral and overbased phenates may be used.

The phenates are ordinarily present in the oil to provide from 0.2% to 27% by weight of the total composition. Preferably, the neutral phenates are present from 0.2% to 9% by weight of the total composition and the overbased phenates are present from 0.2% to 13% by weight of the total composition. Most preferably, the overbased phenates are present from 0.2% to 5% by weight of the total composition. Preferred metals are calcium, magnesium, strontium or barium.

The sulfurized alkaline earth metal alkyl phenates are preferred. These salts are obtained by a variety of processes such as treating the neutralization product of an alkaline earth metal base and an alkylphenol with sulfur. Conveniently, the sulfur, in elemental form, is added to the neutralization product and reacted at elevated temperatures to produce the sulfurized alkaline earth metal alkyl phenate.

If more alkaline earth metal base were added during the neutralization reaction than was necessary to neutralize the phenol, a basic sulfurized alkaline earth metal alkyl phenate is obtained. See, for example, the process of Walker et al., U.S. Pat. No. 2,680,096. Additional basicity can be obtained by adding carbon dioxide to the basic sulfurized alkaline earth metal alkyl phenate. The excess alkaline earth metal base can be added subsequent to the sulfurization step but is conveniently added at the same time as the alkaline earth metal base is added to neutralize the phenol.

Carbon dioxide and calcium hydroxide or oxide are the most commonly used material to produce the basic or "overbased" phenates. A process wherein basic sulfurized alkaline earth metal alkylphenates are produced by adding carbon dioxide is shown in Hanneman, U.S. Pat. No. 3,178,368.

The Group II metal salts of dihydrocarbyl dithiophosphoric acids exhibit wear, antioxidant and thermal stability properties. Group II metal salts of phosphorodithioic acids have been described previously. See, for example, U.S. Pat. No. 3,390,080, Columns 6 and 7, wherein these compounds and their preparation are described generally. Suitably, the Group II metal salts of the dihydrocarbyl dithiophosphoric acids useful in the lubricating oil composition of this invention contain from about 4 to about 18 carbon atoms in each of the hydrocarbyl radicals and may be the same or different and may be aromatic, alkyl or cycloalkyl. Preferred hydrocarbyl groups are alkyl groups containing from 4 to 8 carbon atoms and are represented by butyl, isobutyl, sec-butyl, hexyl, isohexyl, octyl, 2-ethylhexyl, p-tolyl, xylyl and the like. The metals suitable for forming these salts include barium, calcium, strontium, zinc and cadmium, of which zinc is preferred.

Preferably, the Group II metal salt of a dihydrocarbyl dithiophosphoric acid has the following formula:

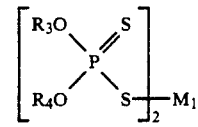

wherein $R_3$ and $R_4$ each independently represent hydrocarbyl radicals as described above, and M1 represents a Group II metal cation as described above.

The dithiophos-phoric salt is present in the lubricating oil compositions of this invention in an amount effective to inhibit wear and oxidation of the lubricating oil. The amount ranges from about 0.1% to about 4% by weight of the total composition, preferably the salt is present in an amount ranging from about 0.2% to about 2.5% by weight of the total lubricating oil composition. The final lubricating oil composition will ordinarily contain 0.025% to 0.25% by weight phosphorus and preferably 0.05% to 0.15% by weight.

The finished lubricating oil may be single or multigrade. Multigrade lubricating oils are prepared by adding viscosity index (VI) improvers. Typical viscosity index improvers are polyalkyl methacrylates, ethylene propylene copolymers, styrene-diene copolymers and the like. So-called decorated VI improvers having both viscosity index and dispersant properties are also suitable for use in the formulations of this invention.

The lubricating oil used in the compositions of this invention may be mineral oil or synthetic oils of lubricating viscosity and preferably suitable for use in the crankcase of an internal combustion engine. Crankcase lubricating oils ordinarily have a viscosity of about 1300 cSt at 0° F. to 22.7 cSt at 210° F. (99° C.) The lubricating oils may be derived from synthetic or natural sources. Mineral oil for use as the base oil in this invention includes paraffinic, naphthenic and other oils that are ordinarily used in lubricating oil compositions Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_6-C_{12}$ alpha olefins such as 1-decene trimer. Likewise, alkyl benzenes of proper viscosity, such as didodecyl benzene, can be used. Useful synthetic esters include the esters of both monocarboxylic acid and polycarboxylic acids as well as monohydroxy alkanols and polyols. Typical examples are didodecyl adipate, pentaerythritol tetracaproate, di-2-ethylhexyl adipate, dilaurylsebacate and the like. Complex esters prepared from mixtures of monoand dicarboxylic acid and mono- and dihydroxy alkanols can also be used.

Blends of hydrocarbon oils with synthetic oils are also useful. For example, blends of 10 to 25 weight percent hydrogenated 1-decene trimer with 75 to 90 weight percent 50 SUS (100° F.) mineral oil gives an excellent lubricating oil base.

Other additives which may be present in the formulation (or in the concentrate referred to above) include rust inhibitors, foam inhibitors, corrosion inhibitors, metal deactivators, pour point depressants, antioxidants, and a variety of other well-known additives.

The following examples are offered to specifically illustrate the invention. These examples and illustrations are not to be construed in any way as limiting the scope of the invention.

EXAMPLES

Example 1

Preparation of $C_{18}$–$C_{24}$ Alkyl Catechol by Batch Process

A 30-gallon reactor equipped with a stirrer, condenser, Dean-Stark trap, and nitrogen inlet and outlet, was charged with 61.67 pounds of $C_{18}$–$C_{24}$ olefins (less than $C_{14}$, 2.7%; $C_{14}$, 0.3%; $C_{16}$, 1.3%; $C_{18}$, 8.0%; $C_{20}$, 44.4%; $C_{22}$, 29.3%; $C_{24}$, 11.2%; $C_{26}$ and above, 2.8%) containing at least 40% branched olefins (available from Ethyl Corp.), 18.32 pounds catechol, 8.0 pounds sulfonic acid cation exchange resin (polystyrene cross-linked with divinylbenzene) catalyst (Amberlyst-15, available from Rohm and Haas, Philadelphia, Pa.), and 9 gallons of Chevron 350H thinner With a stirrer set at 150 rpm, the reaction was carried out at 141° C.–143° C. for a total of 14.7 hours. The reaction mixture was stripped by heating at 143° C. under vacuum (50 mm Hg) for 4 hours. The product was filtered hot over diatomaceous earth to afford 67.21 pounds of a liquid $C_{18}$–$C_{24}$ alkyl catechol. The product contained 1.4% of unreacted catechol by infrared analysis, a hydroxyl number of 199 mg KOH/g, and a low sediment level of 0.02 vol %. Chromatographic analysis showed the product to contain 2.6% of Chevron 350H thinner, 7.4% unreacted olefin, 45.2% monoalkyl catechols, and 44.8% dialkyl catechols.

Example 2

Boration of $C_{18}$–$C_{24}$ Alkyl Catechol p A 3-liter, three-necked, round-bottomed glass flask, equipped with a stirrer, condenser, Dean-Stark trap, and nitrogen inlet, was charged with 860 g of $C_{18}$–$C_{24}$ alkyl catechols prepared according to Example 1, 79.1 g boric acid, and 1200 ml toluene. The reaction mixture was heated under reflux, while stirring, at 115° C.–125° C., collecting a total of 50 g of water in the trap in 6 hours. The reaction mixture was then stripped of solvent by heating at 135° C. under vacuum (20–25 mm Hg) for 3 hours to give 850 g of a liquid, borated $C_{18}$–$C_{24}$ alkyl catechol.

Analysis for boron gave a value of 1.3%, and a measured viscosity at 100° C. of 27 cSt. Exposure of a small sample of product to atmospheric moisture, resulted in boric acid formation on the surface in a matter of seconds. In less than one day the material was hazy and crusted on top. This product was prepared using 3 moles of catechol per 2 moles of boron and the product is believed to have the structure shown in Formula V above.

Amine Treatment of Borated $C_{18}$–$C_{24}$ Alkyl Catechol

A series of runs were made wherein different monoalkylamines were complexed with the borated $C_{18}$–$C_{24}$ alkyl catechol prepared according to Example 2 above.

In each of these runs, which are summarized in Table I below, 10 to 100 g of the borated $C_{18}$–$C_{24}$ alkyl catechol prepared according to Example 2 above was added to a three-necked, round-bottomed glass flask, equipped with a stirrer, condenser, and an addition funnel.

While vigorously stirring, an equimolar amount of the corresponding monoalkylamien was added (1 mole N per 1 mole B) to the alkyl catechol over a period of 1 hour, maintaining a temperature during addition below 50° C. When amine addition was completed, the reaction mixture was stirred at 50° C. for 1 hour, and then heated to 135° C. under vacuum (20–25 mm Hg) for 1 hour to remove unreacted amine, and any toluene which may have been added to facilitate mixing and provide a better contact between the reactants.

TABLE I

| | Monoalkylamine Stabilized Borates | | |
|---|---|---|---|
| Example Number | Amine | Borate C:B[1] | Hydrolytic Stability Rating[2] |
| 3 | 2-Ethylhexylamine | 3:2 | 6 |
| 4 | Cyclohexylamine | 3:2 | 6 |
| 5 | n-Butylamine | 3:2 | 6 |
| 6 | Ethylamine | 3:2 | 6 |
| 7 | Hydroxyethylamine | 3:2 | 6 |
| 8 | Methylamine | 3:2 | 1 |
| 9 | Ammonia | 3:2 | 3 |
| 10 | Benzylamine | 3:2 | 4 |

[1] Catechol to Boron mole ratio in preparing borate.
[2] 1 = Extensive, immediate hydrolysis.
2 = Some immediate hydrolysis.
3 = Hydrolysis within one day.
4 = Hydrolysis within one to three days.
5 = Hydrolysis within three to seven days.
6 = Stable to atmospheric moisture for at least seven days. Examples 3–7 were actually stable for more than six months.

Referring to Table I, Examples 3–7 used the monoalkylamines in accordance with this invention and were hydrolytically stable for at least seven days. Examples 8 and 10 are monoalkylamines which do not fit within the definition of the monoalkylamines of this invention and are unsuitable. Example 9 used ammonia which was also unsuitable.

Oxidation Bench Tests

A series of oxidation bench tests were carried out which demonstrate the improvements in antioxidancy of additives prepared according to Examples 3–7.

The oxidation tests were carried out at 171° C. in a glass reactor and the time required for the sample to consume 1 liter of oxygen was recorded The formulation.contained 1% of additive to be tested, 3.5% of dispersant, 50 mmol/kg of sulfonate, 17 mmol/kg of zinc dialkyldithiophosphates and 6.8% of viscosity index improver in Chevron 100N base oil. The oxidation test was carried out in the presence of metal catalysts normally found in used oil analysis such as Fe, Cu, Pb, Mn, and Cr (see U.S. Pat. 2,883,412 or U.S. Pat. 3,682,980). For comparison basis, a reference run was carried out under identical conditions using the same formulation, but containing no additive to be tested. The results are summarized in Table II.

TABLE II

| OXIDATOR B BENCH TEST PERFORMANCE RESULTS | | | | |
|---|---|---|---|---|
| EXAMPLE NUMBER | ADDITIVE | ADDITIVE CONC., WT % | OXYGEN UPTAKE HR TO 1 L | HOURS IMPROVEMENT |
| 11 | None | — | 12 | — |
| 12 | Example 3 | 1.0 | 16 | 4 |
| 13 | Example 4 | 1.0 | 17 | 5 |
| 14 | Example 5 | 1.0 | 17 | 5 |

TABLE II-continued
OXIDATOR B BENCH TEST PERFORMANCE RESULTS

| EXAMPLE NUMBER | ADDITIVE | ADDITIVE CONC., WT % | OXYGEN UPTAKE HR TO 1 L | HOURS IMPROVEMENT |
| --- | --- | --- | --- | --- |
| 15 | Example 6 | 1.0 | 18 | 6 |
| 16 | Example 7 | 1.0 | 18 | 6 |

Referring to Table II, a reference run (Example 11), without an antioxidant, required 12 hours for the sample to take up one liter of oxygen. Adding as little as 1% of the borated, and primary amine stabilized, additives of this invention (Examples 12-16) led to a substantial improvement in oxidative stability of the formulated oil blend by a factor of 4 to 6 hours, demonstrating the effectiveness of additives of this invention to function as antioxidants.

Example 17

Preparation of Alpha-Olefin Oligomer

A sample of unhydrogenated $C_{30}$ to $C_{50}$ 1-decene oligomers was obtained using procedures essentially the same as those described in U.S. Pat. No. 4,045,507. The sample had a boiling point above 215° C. at 0.5 mm Hg and contained the following olefins, as determined using supercritical fluid chromatography $C_{30}$, 14%; $C_{40}$, 64%; and $C_{50}$, 22% (number average carbon number $C_{41}$). Analysis by NMR for olefin type showed 95% branched olefins

Example 18

Alkylation of Catechol with Alpha-Olefin Oligomer Mixture

A mixture of catechol (19.3 grams), the olefin mixture of Example 17 (100 grams), and triflic acid (2 grams) was heated while stirring for 6 hours at 140° C. The reaction mixture was cooled, taken up in n-hexane (200 ml) and extracted several times with 100 ml portions of aqueous 2-propanol (75/25) to remove the acid and any unreacted catechol. After drying over anhydrous sodium sulfate, the product was filtered and then stripped under high vacuum (about 0.5 mm Hg) at 120-135° C. for 45 minutes to give 111 grams of dark amber alkyl catechol as an oil. This product gave a hydroxyl number of 105 mg KOH/gram sample, which corresponds to about 65% yield based on the catechol.

Example 19

Boration of Product From Example 18

The alkyl catechol prepared in Example 18 (105.6 grams) and boric acid (4.1 grams) were reacted by heating, while stirring, at reflux in toluene (100 ml) and collecting the water formed in a Dean-Stark trap. After refluxing for 3 hours, a total of 3.0 grams of water was recovered, although water formation stopped after 2 hours. Since no solids were visible, the reaction mixture was not filtered, and toluene was stripped to give about 106 grams of borated alkyl catechol, which was a fluid at room temperature. Exposure of a small sample of the purple borated alkylcatechol to atmospheric moisture led to formation of a boric acid crust on the surface of the sample, indicating that the boration reaction had occurred and that the product was hydrolytically unstable. The borated alkyl catechol was stored under nitrogen for oxidation bench tests and amine stabilization experiments.

Example 20

Stabilization of Borated Alkyl Catechol from Example 19 with Propylamine

A mixture of borated alkyl catechol prepared in Example 19 (10 grams) and n-propylamine (1 gram) in toluene (15 ml) was stirred at room temperature for 0.5 hours. The reaction mixture was then refluxed at 110° C. for 1 hour and then stripped of solvent by heating to about 130° C. at 0.5 mm Hg to give 10.8 grams of a dark amber oil, with a purplish cast. Exposure of a small sample of product to atmospheric moisture showed no haze or precipitate formation after standing uncovered in a petri dish exposed to air for over 30 days.

Oxidation Bench Tests

A series of oxidation bench tests were carried out which demonstrate the antioxidancy of the additive prepared according to Example 20.

The oxidation tests were conducted using the procedures described in R. W. Dornte, "Oxidation of White Oils," *Industrial and Engineering Chemistry*, 28, p. 26 (1936). The formulation contained 2% by weight of the additive to be tested, 3.5% of dispersant, 50 mmol/kg of calcium as sulfonate, 17 mmol/kg of zinc dialkyl dithiophosphate, and 6.8% of viscosity index improver in Chevron 100N base oil. The oxidation test was carried out at 171° C. in a glass reactor in the presence of metal catalysts normally found in used oil (from the Sequence IIE engine test), such as Fe, Cu, Pb, Mn, and Cr (added as napthenates). The time required for the sample to consume 1 liter of oxygen was recorded. For comparison purposes, a reference run was carried out under identical conditions using the same formulation, but containing no additive to be tested. The results are summarized in Table III.

TABLE III
OXIDATOR AO BENCH TEST PERFORMANCE RESULTS

| EXAMPLE NUMBER | ADDITIVE | ADDITIVE CONC., WT % | OXYGEN UPTAKE HR TO 1 L | HOURS IMPROVEMENT |
| --- | --- | --- | --- | --- |
| 21 | None | — | 7.8 | — |
| 22 | Example 19 | 2.0 | 27.3 | 20 |
| 23 | Example 20 | 2.0 | 24.6 | 17 |

Referring to Table III above, a reference run (Example 21), without an antioxidant additive, required 7.8 hours for the sample to take up one liter of oxygen. Adding 2 weight percent of the additives of Examples 19 and 20 led to a substantial improvement in the oxidative stability of the formulated oil blend, demonstrating the effectiveness of additives of this invention as antioxidants. The slightly better antioxidancy of the formulated oil blend containing the borated product of Example 19 (Example 22 in Table III) as compared to the formulated oil blends containing the amine-stabilized product of Example 20 (Example 23 in Table III) may, in part, be attributed to the diluation effect of the boron level by the amine.

It is to be understood that various modifications of the present invention will occur to those skilled in the art upon reading the foregoing disclosure. It is intended that all such modifications be covered which reasonably fall within the scope of the appended claims. For example, it is within the purview of the present invention to use the defined monoalkylamines to stabilize a borated alkyl catechol which has been partially stabilized with some other stabilizing agent such as succinimide or, perhaps, another amine.

What is claimed is:

1. A composition comprising a complex of a borated alkyl catechol and an amount to hydrolytically stabilize the. borated alkyl catechol of one or mroe monoalkylamines or monoalkanomines having from 2 to 10 carbon atoms and from 0 to 3 hydroxyl groups; wherein said borated alkyl catechol has a molar ratio of alkyl catechol to boron of 1:1 or 3:2 or mixtures thereof and further wherein the alkyl group of said borated alkyl catechol contains at least 10 carbon atoms.

2. The composition according to claim 1 wherein said alkyl group of said borated alkyl catechol contains 32 to 60 carbon atoms.

3. The composition according to claim 1 wherein said borated alkyl catechol is a mixture of borated alkyl catechols having alkyl groups of different carbon number and further wherein said alkyl groups have a number average carbon number of 35 to 45.

4. The composition Cl 1 wherein the amount of monoalkylamine or monoalkanolamine is at least about 0.8 moles of monoalkylamine or monoalkanolamine per mole of boron.

5. The composition according to claim 4 wherein the molar ratio of monoalkylamine or monoalkanolamine to boron is about 0.8:1 to about 1.1:1.

6. The composition according to claim 1 wherein said mixture of borated alkyl catechol consists essentially of borated alkyl catechol having an alkyl catechol to boron mole ratio of 3:2.

7. A composition comprising a complex of a borated alkyl catechol and an amount to hydrolytically stabilize the borated alkyl catechol of one or more monoalkylamines or monoalkanomines having the formula:

where R' is an aliphatic hydrocarbon radical having from 2 to 10 carbon atoms and optionally containing 1 to 3 hydroxyl groups, or an alicyclic hydrocarbon radical having 5 or 6 carbon atoms; wherein said borated alkyl catechol has a molar ratio of alkyl catechol to boron of 1:1 or 3:2 or mixtures thereof and further wherein the alkyl group of said borated alkyl catechol contains at least 10 carbon atoms.

8. The composition according to claim 7 wherein said alkyl group of said borated alkyl catechol contains 32 to 60 carbon atoms.

9. The composition according to claim 8 wherein said alkyl group of said borated alkyl catechol contains 36 to 50 carbon atoms.

10. The composition according to claim 7 wherein said borated alkyl catechol is a mixture of borated alkyl catechols having alkyl groups of different carbon number and further wherein said alkyl groups have a number average carbon number of 35 to 45.

11. The composition according to claim 7 wherein teh amount of monoalkylamine or monoalkanolamine is at least about 0.8 moles of monoalkylamine or monoalkanolamine per mole of boron.

12. The composition according to claim 11 wherein the molar ratio of monoalkylamine or monoalkanolamine to boron is about 0.8:1 to about 1.1:1.

13. The composition according to claim 7 wherein said borated alkyl catechol consists essentially of borated alkyl catechol having an alkyl catechol to boron mole ratio of 3:2.

14. The composition according to claim 13 wherien the molar ratio of monoalkylamine or monoalkanolamine to boron is about 1:1.

15. The composition according to claim 7 wherein the borated alkyl catechol has from one to two alkyl groups and each alkyl group has from 32 to 60 carbon atoms.

16. The composition according to claim 7 wherein the monoalkylamine or monoalkanolamine is selected from the group consisting of 2-ethylhexylamine; cyclohexylamine; ethylamine; n-butylamine; and hydroxyethylamine.

17. A product prepared by the process which comprises:
(a) forming a borated alkyl catechol wherein said borated alkyl catechol has a molar ratio of alkyl catechol to boron of 1:1 or 3:2 or mixtures thereof and further wherein said alkyl group of said borated alkyl catechol contains at least 10 carbon atoms; and
(b) contacting said borated with one or more monoalkylamines or monoalkanolamines having the formula:

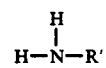

where R' is an aliphatic hydrocarbon radical having from 2 to 10 carbon atoms and optionally containing 1 to 3 hydroxyl groups, or an alicyclic hydrocarbon radical having 5 or 6 carbon atoms; under conditions wherein a complex is formed between the monoalkylamine or monoalkanolamine and the borated alkyl catechol, the amount of said monoalkylamine or monoalkanolamine being sufficient to stabilize said borated alkyl catechol against hydrolysis.

18. The product prepared by the process according to claim 17 wherein said alkyl group of said borated alkyl catechol contains 32 to 60 carbon atoms.

19. The product prepared by the process according to claim 17 wherein said borated alkyl catechol is a mixture of borated alkyl catechols having alkyl groups of different carbon number and further wherein said alkyl groups have a number average carbon number of 35 to 45.

20. A method to hydrolytically stabilize a borated alkyl catechol which comprises contacting said borated alkyl catechol with a hydrolytically stabilizing amount of one or more monoalkylamines or monoalkanolamines having the formula:

where R' is an aliphatic hydrocarbon radical having from 2 to 10 carbon atoms and optionally containing 1 to 3 hydroxyl groups, or an alicyclic hydrocarbon radical having 5 or 6 carbon atoms; under conditions wherein a complex is formed between said monoalkylamine or monoalkanolamine and said borated alkyl catechol; wherein said borated alkyl catechol has a molar ratio of alkyl catechol to boron of 1:1 or 3:2 or mixtures thereof and further wherein said alkyl group of said borated alkyl catechol contains at least 10 carbon atoms.

21. The method according to claim 20 wherein the molar ratio of monoalkylamine or monoalkanolamine to boron 0.8:1 to about 1.1:1.

22. The method according to claim 21 wherein said alkyl group of said borated alkyl catechcol contains 32 to 60 carbon atoms.

23. The method according to claim 21 wherein said borated alkyl catechol is a mixture of borated alkyl catechols having alkyl groups of different carbon number and further wherein said alkyl groups have a number average carbon number of 35 to 45.

24. The method according to claim 21 wherein said borated alkyl catechol consists. essentially of borated alkyl catechol having an alkyl catechol to boron mole ratio of 3:2.

25. The method according to claim 20 wherein said complex is formed in the presence of a solvent and at a temperature of about 30° C. to about 100° C.

26. A lubricating oil composition comprising a major amount of an oil of lubricating viscosity and a minor amount of a hydrolyticall borated alkyl catechol-monoalkylamine monoalkylamine or monoalkanolamine complex wherein borated alkyl catechol of said complex has an alkyl catechol to boron mole ratio of 1:1 or 3:2 or mixtures thereof and further wherein the alkyl group of said borated alkyl catechol contains at least 10 carbon atoms; and wherein the monoalkylamine or monoalknaolamine of said complex has the formula:

where R' is an aliphatic hydrocarbon radical having from 2 to 10 carbon atoms and optionally containing 1 to 3 hydroxyl groups, or an alicyclic hydrocarbon radical having 5 or 6 carbon atoms.

27. The lubricating oil composition according to claim 26 wherein the amount of said complex is from 0.05% to 20% by weight of said composition.

28. The lubricating oil composition according to claim 27 wherein said alkyl group of said borated alkyl catechol contains 32 to 60 carbon atoms.

29. The lubricating oil composition according to claim 28 wherein said alkyl group of said borated alkyl catechol contains 36 to 50 carbon atoms.

30. The lubricating oil composition according to claim 27 wherein said borated alkyl catechol is a mixture of borated alkyl catechols having alkyl groups of different carbon number and further wherein said alkyl groups have a number average carbon number of 35 to 45.

31. The lubricating oil composition accordin claim 27 wherein the amount of monoalkylamine or monoalkanolamine is at least about 0.8 moles of monoalkylamine or monoalkanolamine per mole of boron.

32. The lubricating oil composition according to claim 31 wherein the molar ratio of monoalkylamine or monoalkanolamine to boron is about 0.8:1 to about 1.1:1.

33. The lubricating oil composition according to claim 32 wherein said borated alkyl catechol consists essentially of borated alkyl catechol having an alkyl catechol to boron mole ratio of 3:2.

34. The lubricating oil composition according to claim 27 wherein the monoalkylamine or monoalkanolamine is selected from the group consisting of 2-ethylhexylamine; cyclohexylamine; ethylamine; n-butylamine; and hydroxyethylamine 35. A method for reducing oxidation and deposits during operation of an internal combustion engine comprising operating said internal combustion engine with a lubricating oil composition according to claim 26.

36. A lubricating oil concentrate comprising a neutral carrier oil and from about 5 to about 80 weight percent of a hydrolytically stable borated alkyl catechol-monoalkylamine or monoalkanolamine complex wherein the borated alkyl catechol of said complex has an alkyl catechol to boron mole ratio of 1:1 or 3:2 or mixtures thereof and further wherein the alkyl group of said borated alkyl catechol contains at least 10 carbon atoms; and wherein the monoalkylamine or monoalkanolamine of has the formula:

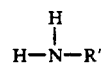

where R' is an aliphatic hydrocarbon radical having from 2 to 10 carbon atoms and optionally containing 1 to 3 hydroxyl groups, or an alicyclic hydrocarbon radical having 5 or 6 carbon atoms.

37. The lubricating oil concentrate according to claim 36 wherein said alkyl group of said borated alkyl catechol contains 32 to 60 carbon atoms.

38. The lubricating oil concentrate according to claim 36 wherein said borated alkyl catechol is a mixture of borated alkyl catechols having alkyl groups of different carbon number and further wherein said alkyl groups have a number average carbon number of 35 to 45.

39. The lubricating oil concentrate according to claim 36 wherein the molar ratio of monoalkylamine or monoalkanolamine to born is about 0.8:1 to about 1 1:1.

40. The lubricating oil concentrate according to claim 36 wherein said mixture of borated alkyl catechol consists essentially of borated alkyl catechol having an alkyl catechol to boron mole ratio of 3:2.

41. The lubricating oil concentrate according to claim 36 wherein the monoalkylamine or monoalkanolamine is selected from the group consisting of 2-ethylhexylamine; cyclohexylamine; ethylamine; n-butylamine; and hydroxyethylamine.

* * * * *

UNITED STATES PATENT AND TRADEMARK OFFICE
CERTIFICATE OF CORRECTION

PATENT NO. : 5,160,650

DATED : November 3, 1992

INVENTOR(S) : Vernon R. Small, Jr., Thomas V. Liston, and Anatoli Onopchenko

It is certified that error appears in the above-identified patent and that said Letters Patent is hereby corrected as shown below:

Column 17, line 25, "mroe" should read --more--.

Column 17, line 26, 'monoalkanomines" should read --monoalkanolamines--.

Column 17, line 40, "Cl 1" should read --according to Claim 1--.

Column 17, line 55, "monoalkanomines" should read --monoalkanolamines--.

Column 18, line 13, "teh" should read --the--.

Column 18, line 24, 'wherien" should read --wherein--.

Column 18, line 44, "borated" should read --borated alkyl catechol--.

Column 19, line 25, "boron" should read --boron is about--.

Column 19, line 43, "hydrolyticall" should read --hydrolytically stable--.

Column 19, line 44, "monoalkylamine monoalkylamine" should read --monoalkylamine--.

Column 19, line 45, "wherein" should read --wherein the--.

Column 19, line 50, "monoalknaolamine" should read --monoalkanolamine--.

Column 20, line 7, "accordin" should read --according to--.

Column 20, line 37, "of" should read --of said complex--.

UNITED STATES PATENT AND TRADEMARK OFFICE
CERTIFICATE OF CORRECTION

PATENT NO. : 5,160,650

DATED : November 3, 1992

INVENTOR(S) : Vernon R. Small, et al

Page 2 of 2

It is certified that error appears in the above-indentified patent and that said Letters Patent is hereby corrected as shown below:

Column 20, line 58, "born" should read --boron--.

Signed and Sealed this

First Day of March, 1994

Attest:

BRUCE LEHMAN

Attesting Officer

Commissioner of Patents and Trademarks